United States Patent [19]

Sprecker et al.

[11] Patent Number: 5,137,869
[45] Date of Patent: Aug. 11, 1992

[54] METHYL SUBSTITUTED TETRAHYDROINDANONE AND PERFUMERY USES THEREOF

[75] Inventors: Mark A. Sprecker, Sea Bright; Robert P. Belko, Woodbridge, both of N.J.; Eleanor Fox, New York, N.Y.; Alphonsus P. M. Maas, Sint-Odenrode; Djurre S. Postma, Tilburg, both of Netherlands

[73] Assignee: International Flavors & Fragrances Inc., New York, N.Y.

[21] Appl. No.: 759,916

[22] Filed: Sep. 13, 1991

[51] Int. Cl.$^5$ .............................. A61K 7/46
[52] U.S. Cl. .................. 512/15; 568/374
[58] Field of Search ................. 512/15; 568/374

[56] References Cited

U.S. PATENT DOCUMENTS 3,847,993 11/1974 Hall et al. .................. 512/15
3,927,083 12/1975 Hall et al. .................. 512/15

OTHER PUBLICATIONS

Cooke et al., Tetrahedron Letters, #22, pp. 1995–1998 (1979).

*Primary Examiner*—James H. Reamer
*Attorney, Agent, or Firm*—Arthur L. Liberman

[57] ABSTRACT

Described is the methyl substituted tetrahydroindanone having the structure:

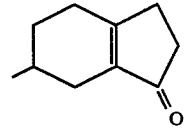

and uses thereof in augmenting or enhancing the aroma of consumable materials selected from the group consisting of perfume compositions, colognes and perfumed articles.

7 Claims, 3 Drawing Sheets

GLC PROFILE FOR EXAMPLE I

NMR SPECTRUM FOR EXAMPLE I

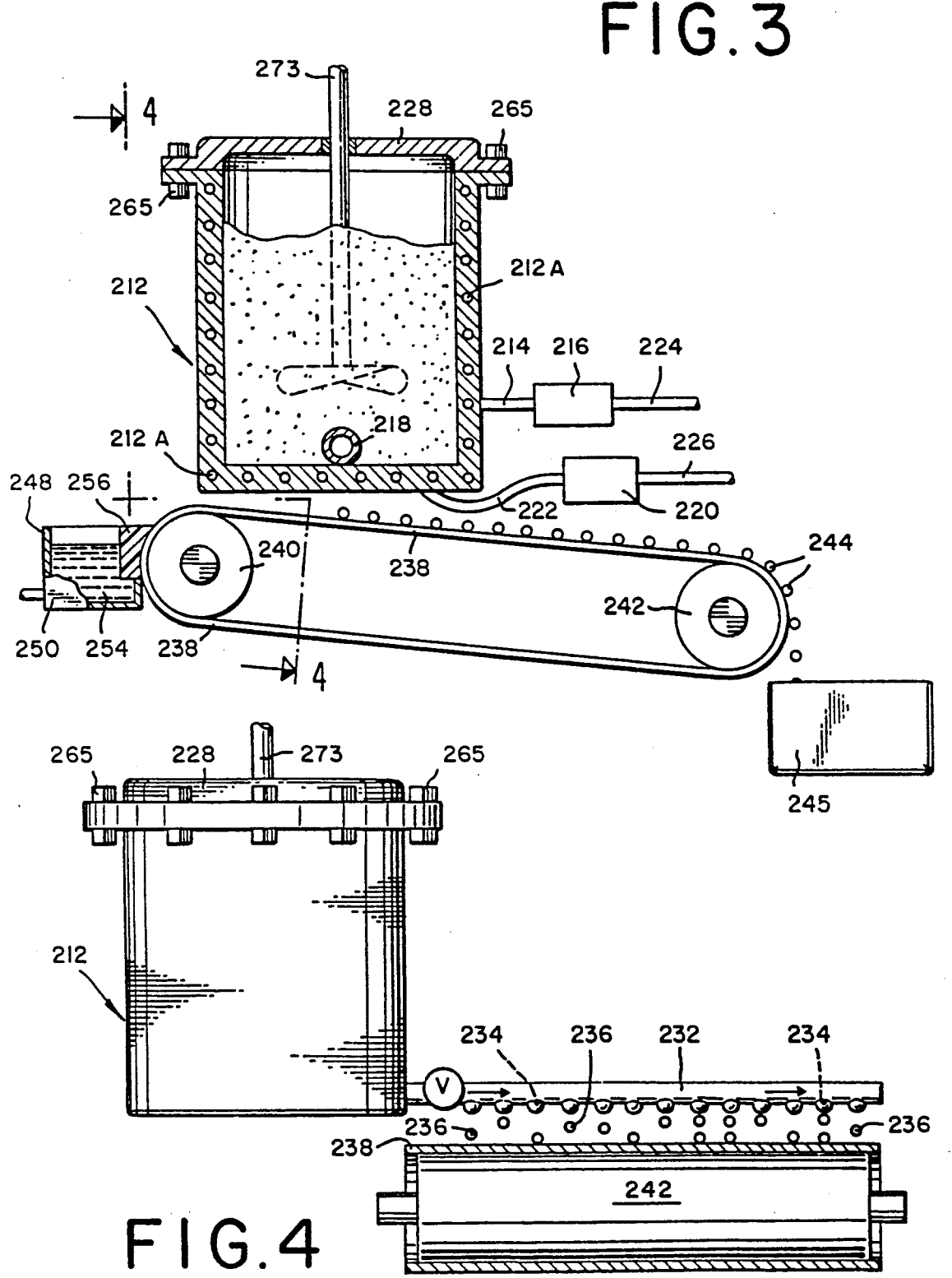

METHYL SUBSTITUTED TETRAHYDROINDANONE AND PERFUMERY USES THEREOF

BACKGROUND OF THE INVENTION

The present invention relates to the methyl substituted tetrahydroindanone defined according to the structure:

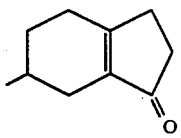

and uses of such methyl substituted tetrahydroindanone in augmenting or enhancing the aroma of perfume compositions, perfumed articles and colognes.

There has been considerable work performed relating to substances which can be used to impart (modify, augment or enhance) fragrances to (or in) various consumable materials. Such substances are used to diminish the use of expensive natural materials some of which may be in short supply and to provide more uniform properties in the finished product.

Sweet, maple, tonka, honey, coumarin-like and cherry aromas, with sweet, honey, coumarin, tonka absolute-like and maple topnotes are particularly desirable in several types of perfume compositions, perfumed articles and colognes.

The use of bicyclicindanones in perfumery is known in the prior art. Thus, Arctander ("Perfume and Flavor Chemicals" (Aroma Chemicals)), Volume I, 1969, at Monograph 1710 discloses the use of the compound having the structure

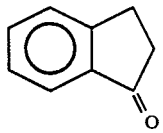

in augmenting or enhancing the aroma of perfume compositions. Arctander states:

1710: alpha-HYDRINDONE

1-Indanone.
1-Ketoindane.

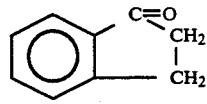

$C_9H_8O$ = 132.16
Rhombic colorless crystal needles, melting at 41° C. BP. 244° C.
Sp. Gr. 1.10 (liquid).
Slightly soluble in water, soluble in alcohol, miscible with oils.

Rather weak, woody and somewhat medicinal odor with an incense-like undertone. It may be because of its remote resemblance to incense, that this odor has caught any interest at all. Apart from that, there is not much to be said, except that the material could be of academic interest for olfactory studies. The author believes that subject ketone is rarely, if ever, used in perfumes or flavors.
Prod.: by cyclization of beta-Phenyl-propionyl chloride in Benzene.
4-63; 26-576; 68-1265; 160-1050; B-VII-360;

Arctander, however, does not disclose the unobvious, unexpected and advantageous perfumery properties of the methyl substituted tetrahydroindanone of our invention.

Tetrahydroindanone compounds are known per se but not for their uses in perfumery. Thus, Chem. Abstracts, Volume 93, No. 149841c (abstract of Hiyama, et al, Bull. Chem. Soc. Jpn. 1980, 53(4), 1010-14) discloses the synthesis of the compounds having the structures:

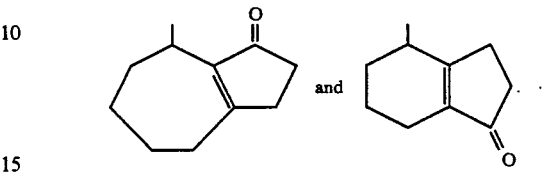

Chem. Abstracts, Volume 79, No. 115200p discloses the synthesis of the compound having the structure:

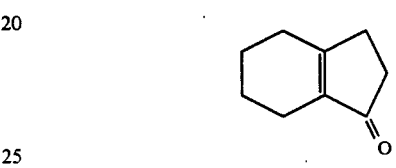

(abstract of Bishop, Tetrahedron Lett. 1973, (26), 2375-6).

Chem. Abstracts, Volume 52, No. 1976g (abstract of Sukh Dev, J. Indian Chem. Soc. 34, 169-77 (1957) discloses the synthesis of the compounds having the structures:

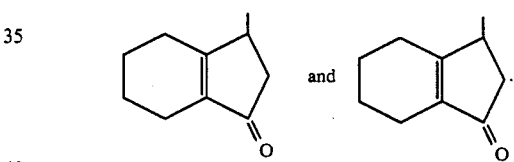

The compound having the structure:

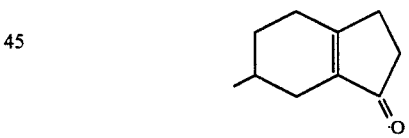

has unexpected, unobvious and advantageous perfumery properties when compared to compounds having the structures:

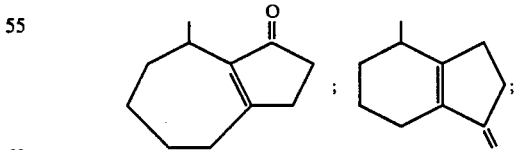

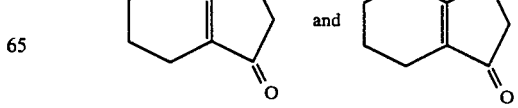

as well as the compound having the structure:

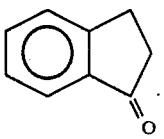

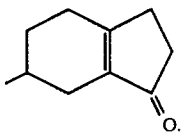

Figure 2:
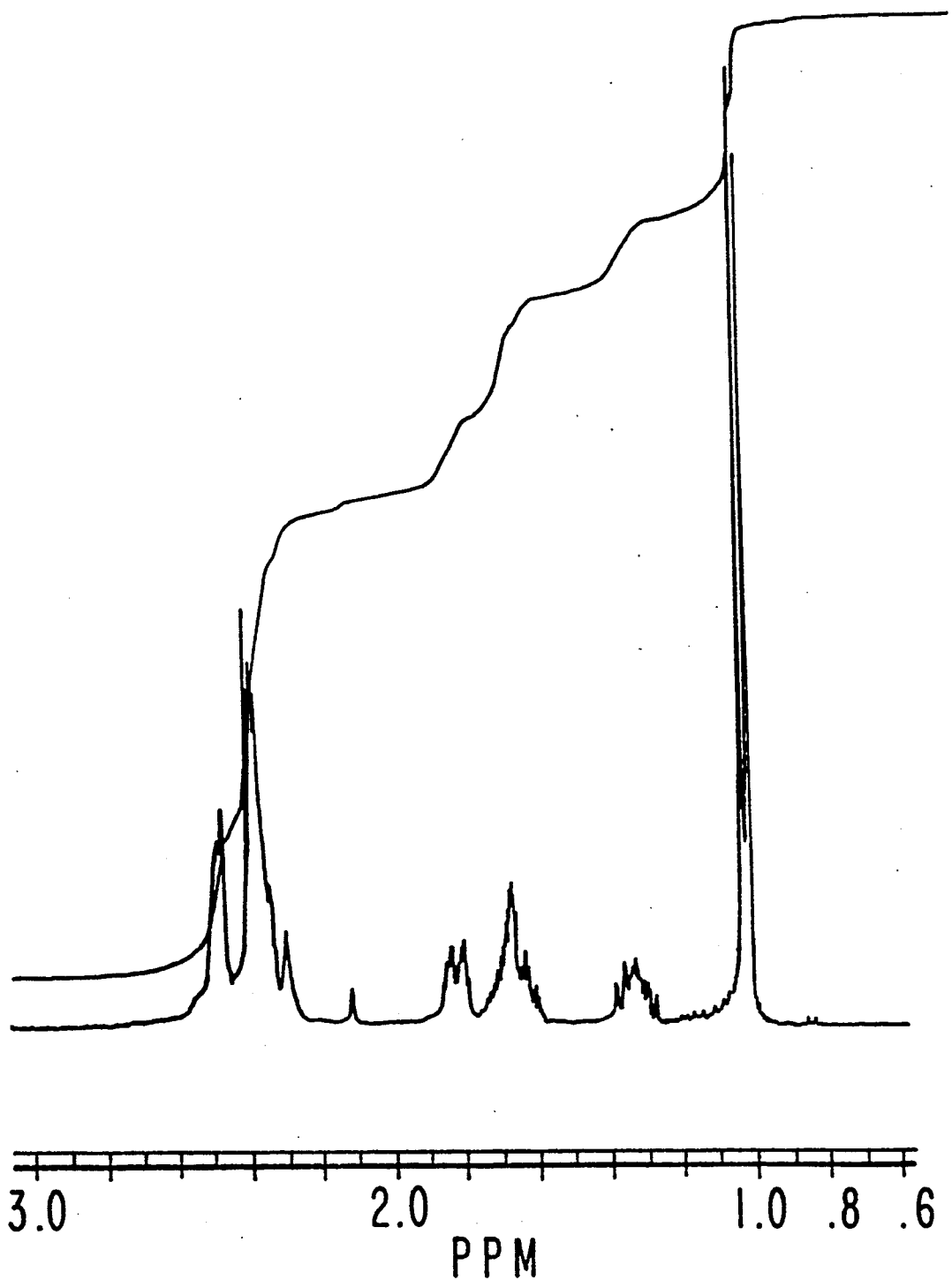

FIG. 2 is the NMR spectrum for the compound having the structure:

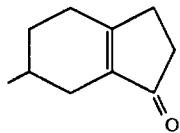

prepared according to Example I.

FIG. 3 represents a cut-away side elevation view of apparatus used in forming perfumed polymers which contain imbeded therein the methyl substituted tetrahydroindanone of our invention.

FIG. 4 is a front view of the apparatus of FIG. 3 looking in the direction of the arrows.

DETAILED DESCRIPTION OF THE DRAWINGS

Figure 1:
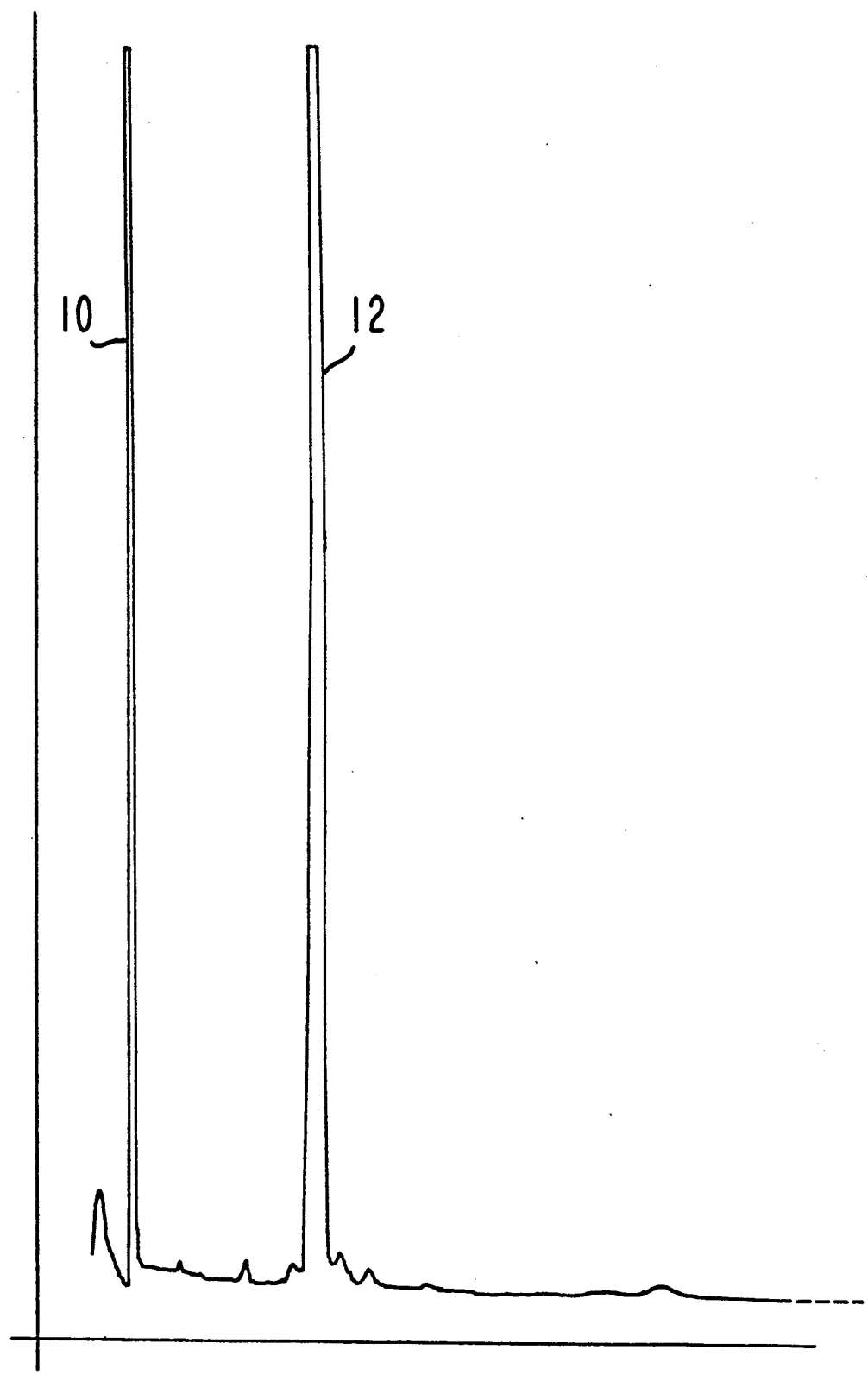
FIG. 1 is the GLC profile for the reaction product of Example I containing the compound having the structure.

Referring to FIG. 1, the peak indicated by reference numeral 12 is the peak for the compound having the structure:

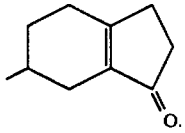

The peak indicated by reference numeral 10 is the peak for the solvent used in the reaction (Conditions: SE-30 column programmed at 180° C. isothermal).

Referring to FIGS. 3 and 4, there is provided a process for forming scented polymer elements (wherein the polymer may be a thermoplastic polymer such as low density polyethylene or polypropylene or copolymers of ethylene and vinyl acetate or mixtures of polymers and copolymers such as copolymers of ethylene and vinyl acetate and polyethylene) such as pellets useful in the formation of plastic particles useful in fabricating certain articles which may be perfumed. This process comprises heating the polymer or mixture of polymers to the melting point of said polymer or mixture of polymers, e.g., 250° C. in the case of low density polyethylene. The lower most portion of the container is maintained at a slightly lower temperature and the material in the container is taken off at such location for delivery through the conduit. Thus, referring ring to FIGS. 3 and 4, in particular, the apparatus used in producing such elements comprises a device for forming the polymer containing perfume, e.g., polyethylene or polyethylene-polyvinyl acetate or mixtures of same or polypropylene, which comprises a vat or container 212 into which the polymer taken alone or in admixture with other copolymers and the perfuming substance which is the methyl substituted tetrahydroindanone of our invention or mixtures of the methyl substituted tetrahydroindanone of our invention and compatible perfumes is placed. The container is closed by means of an airtight lid 228 and clamped to the container by bolts 265. A stirrer 273 traverses the lid or cover 228 in an air-tight manner and is rotatable in a suitable manner. A surrounding cylinder 212A having heating coils which are supplied with electric current through cable 214 from a rheostat or control 216 is operated to maintain the temperature inside the container 212 such that the polymer in the container will be maintained in the molten or liquid state. It has been found advantageous to employ polymers at such a temperature that the viscosity will be in the range of 90–100 sayboldt seconds. The heater 218 is operated to maintain the upper portion of the container 212 within a temperature range of, for example, 220°–270° C. in the case of low density polyethylene. The bottom portion of the container 212 is heated by means of heating coils 212A regulated through the control 220 connected thereto through a connecting wire 222 to maintain the lower portion of the container 212 within a temperature range of 220°–270° C.

Thus, the polymer or mixture of polymers added to the container 212 is heated from 10–12 hours, whereafter the perfume composition or perfume material which contains the methyl substituted tetrahydroindanone of our invention is quickly added to the melt. Generally, about 10–45 percent by weight of the resulting mixture of the perfumery substance is added to the polymer.

After the perfume material is added to the container 212, the mixture is stirred for a number of minutes, for example, 5–15 minutes and maintained within the temperature ranges indicated previously by the heating coil 212A. The controls 216 and 220 are connected through cables 224 and 226 to a suitable supply of electric current for supplying the power for heating purposes.

Thereafter, the valve "V" is opened permitting the mass to flow outwardly through conduit 232 having a multiplicity of orifices 234 adjacent to the lower side thereof. The outer end of the conduit 232 is closed so that the liquid polymer in intimate admixture with the methyl substituted tetrahydroindanone of our invention or mixture of methyl substituted tetrahydroindanone of our invention and one or more other substances, will continuously drop through the orifices 234 downwardly from the conduit 232. During this time, the temperature of the polymer intimately admixed with the perfumery substance in the container 212 is accurately controlled so that a temperature in the range of from about 240°–250° C., for example, (in the case of low density polyethylene) will exist in the conduit 232. The regulation of the temperature through the controls 216 and 220 is essential in order to insure temperature balance to provide for the continuous dripping or dropping of molten polymer intimately admixed with the perfume substance which is all of or which contains the methyl substituted tetrahydroindanone of our invention, through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238 they form pellets 244 which harden almost instantaneously and fall off the end of the conveyor 238 into a container 250 which is advantageously filled with water or some other suitable cooling liquid to insure the rapid cooling of each of the pellets 244. The pellets 244 are then collected from the container 250 and utilized for the formation of other functional products, e.g., garbage bags and the like.

THE INVENTION

The present invention provides the methyl substituted tetrahydroindanone having the structure:

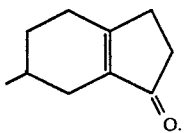

The methyl substituted tetrahydroindanone of our invention having the structure:

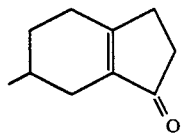

is produced according to a prior art process according to the reaction:

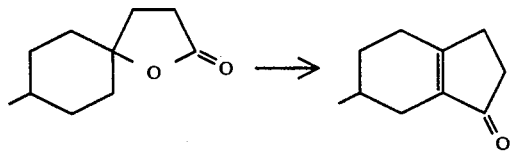

(Reference: Kularni and Dev, "Organic Reactions With Polyphosphoric Acid VIII/Intramolecular Acylation With Lactones (Further Extension), Hydroxy Acids And Esters", Tetrahedron, Vol. 24, pages 553-560).

The process for preparing the compound having the structure:

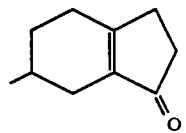

from the compound having the structure:

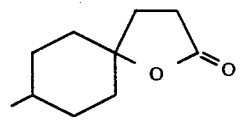

according to the reaction:

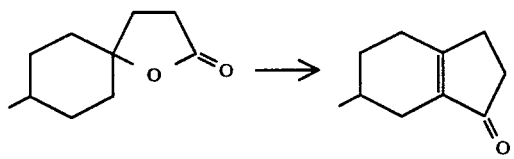

takes place in the presence of polyphosphoric acid at a temperature of about 100° C. for a period of time of about two hours. The resulting reaction product is then washed with base, e.g., aqueous 5% sodium carbonate and then fractionally distilled at a vapor temperature in the range of from 69°-72° C. and a pressure of about 0.8 mm/Hg. as set forth in Example I, infra.

The compound having the structure:

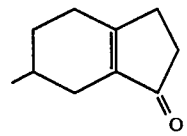

has a sweet, maple, tonka, honey, coumarin-like and cherry aroma, with sweet, honey, coumarin, tonka absolute-like and maple topnotes causing it to be useful as a complete coumarin replacer in perfume formulations.

The methyl substituted tetrahydroindanone of our invention prepared in accordance with the process of the prior art and one or more auxilliary perfume ingredients including, for example, alcohols, aldehydes, ketones other than the methyl substituted tetrahydroindanone of our invention, terpenic hydrocarbons, nitriles, esters, lactones, natural essential oils and synthetic essential oils may be admixed so that the combined odors of the individual components produce a pleasant and desired fragrance, particularly, and preferably, in patchouli fragrances. Such perfume compositions usually contain (a) the main note or the "bouquet" or foundation stone of the composition; (b) modifiers which round out and accompany the main note; (c) fixatives which include odorous substances which lend a particular note to the perfume throughout all stages of evaporation and substances which retard evaporation; and (d) topnotes which are usually low-boiling, fresh-smelling materials.

In perfume compositions, it is the individual components which contribute to their particular olfactory characteristics, however, the overall sensory effect of the perfume composition will be at least the sum total of the effects of each of the ingredients. Thus, the methyl substituted tetrahydroindanone of our invention can be used to alter, modify or enhance the aroma characteristics of a perfume composition, for example, by utilizing or moderating the olfactory reaction contributed by another ingredient in the composition.

The amount of the methyl substituted tetrahydroindanone of our invention which will be effective in perfume compositions as well as in perfumed articles (e.g., anionic, cationic, nonionic or zwitterionic detergents, soaps and fabric softener compositions and articles) and colognes depends on many factors including the other ingredients, their amounts and the effects which are desired. It has been found that perfume compositions containing as little as 0.01% of the methyl substituted tetrahydroindanone of our invention and as much as 50% of the methyl substituted tetrahydroindanone of our invention can be used to impart a sweet, maple, tonka, honey, coumarin-like and cherry aroma, with sweet, honey, coumarin, tonka absolute-like and maple topnotes to soaps, cosmetics, anionic, cationic, nonionic or zwitterionic detergents, fabric softener compositions, fabric softener articles, perfumed polymers and other articles. The amount employed can range up to 70% of the fragrance components and will depend on considerations of cost, nature of the end product, the effect desired on the finished product and the particular fragrance sought.

The methyl substituted tetrahydroindanone of our invention (taken alone or together with other ingredients in perfume compositions) as (an) olfactory component(s) in detergents and soaps, space odorants and deodorants, perfumes, colognes, toilet water, bath preparations, such as creams, deodorants, hand lotions and sun screens; powders, such as talcs, dusting powders, face powders, perfumed polymers and the like. When used as (an) olfactory component(s) as little as 0.2% of the methyl substituted tetrahydroindanone of our invention will suffice to impart an intense and substantive sweet, maple, tonka, honey, coumarin-like and cherry aroma, with sweet, honey, coumarin, tonka absolute-like and maple topnotes to patchouli formulations and to vetiver formulations. Generally, no more than 6% of the methyl substituted tetrahydroindanone of our invention based on the ultimate end product is required in the perfumed article composition. Accordingly, the range of the methyl substituted tetrahydroindanone of our invention in a perfumed article may vary from 0.2% up to about 6% by weight of the ultimate perfumed article.

In addition, the perfume compositions or fragrance compositions of our invention can contain a vehicle or carrier for the methyl substituted tetrahydroindanone of our invention. The vehicle can be a liquid, such as a non-toxic alcohol, e.g., ethyl alcohol, a glycol, e.g., propylene glycol or the like. the carrier can also be an absorbent solid, such as a gum (e.g., gum arabic, xanthan gum or guar gum) or components for encapsulating the composition (such as gelatin as by coacervation or such as a urea-formaldehyde pre-polymer when forming a urea-formaldehyde polymer wall around a liquid perfume center).

It will thus be apparent that the methyl substituted tetrahydroindanone of our invention can be utilized either to alter, modify or enhance sensory properties, particularly organoleptic properties such as fragrances of a wide variety of consumable materials.

The following examples illustrate methods (primarily disclosed in the prior art) used to manufacture the methyl substituted tetrahydroindanone of our invention.

Examples following Example I (Examples II, et seq.) illustrate the organoleptic ultilites of the methyl substituted tetrahydroindanone of our invention.

All parts and percentages given herein are by weight unless otherwise specified.

EXAMPLE I

Preparation of 6-Methylhexahydro-7-Inden-1-One

Reaction:

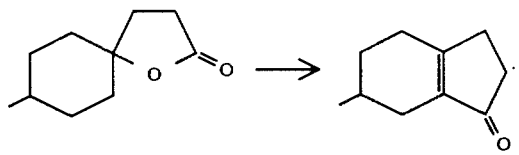

Into a 2 liter reaction flask equipped with stirrer, thermometer, reflux condenser and addition funnel is placed 600 grams of polyphosphoric acid. The polyphosphoric acid is heated to 100° C. with stirring and then over a two hour period 200 grams of the compound having the structure:

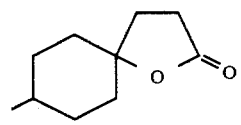

is added to the reaction mass. At the end of the two hour period, the reaction mass is quenched with 300 grams of water followed by an equal volume of 5% aqueous sodium carbonate.

The aqueous phase is separated from the organic phase and the organic phase is distilled on a 12" Goodloe column yielding the following fractions:

| Fraction No. | Vapor Temp. (°C.) | Liquid Temp. (°C.) | Vacuum mm/Hg. Pressure | Reflux Ratio |
|---|---|---|---|---|
| 1 | 23/24 | 68/110 | 2.0 | 9:1/ |
| 2 | 79 | 110 | 1.0 | 9:1 |
| 3 | 69 | 109 | 0.8 | 9:1 |
| 4 | 61 | 109 | 0.8 | 9:1 |
| 5 | 72 | 110 | 0.8 | 9:1 |
| 6 | 72 | 112 | 0.8 | 9:1 |
| 7 | 72 | 115 | 0.8 | 9:1 |
| 8 | 61 | 160 | 0.8 | 9:1. |

Fractions 3-7 are bulked.

Bulked distillation Fractions 3-7 have a sweet, maple, tonka, honey, coumarin-like and cherry aroma, with sweet, honey, coumarin, tonka absolute-like and maple topnotes.

FIG. 1 is the GLC profile for the reaction production prior to distillation. FIG. 2 is the NMR spectrum for the compound having the structure:

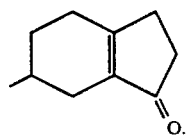

EXAMPLE II

Patchouli Formulation

The following patchouli formulation is produced:

| Ingredients | Parts by Weight |
| --- | --- |
| 4-Hydroxy-tricyclo[3.3.1.1] 2-methylene decane acetate prepared according to Example V of U.S. Letters Patent 4,985,403 | 52 |
| Patchouli oil distilled | 23 |
| Sandalwood oil, E.I. | 12 |
| Vetiver oil-Bourbon | 06 |
| Clove Oil | 28 |
| Geranium oil Algerian | 52 |
| Benzyl acetate | 61 |
| The compound having the structure: 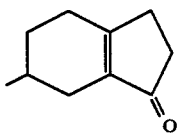 | 12 |

The compound having the structure:

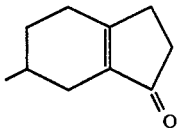

imparts to this patchouli formulation an intense and substantive sweet, maple, tonka-like, honey, coumarin-like and cherry undertone, with sweet, honey, coumarin, tonka absolute-like and maple topnotes. Accordingly, the perfume formulation of this example can be described as "patchouli, with sweet, maple, tonka, honey, coumarin-like and cherry undertones, with sweet, honey, coumarin, tonka absolute-like and maple topnotes".

EXAMPLE III

Preparation of Cosmetic Powder Compositions

Cosmetic powder compositions are prepared by mixing in a ball mill 100 grams of talcum powder with 0.25 grams of each of the substances set forth in Table I below. Each of the cosmetic powder compositions has an excellent aroma as described in Table I below.

TABLE I

| Substance | Aroma Description |
| --- | --- |
| The compound having the structure: 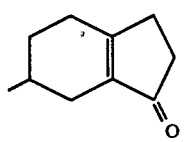 prepared according to Example I, bulked distillation Fractions 3-7. | A sweet, maple, tonka, honey, coumarin-like and cherry aroma, with sweet, honey, coumarin, tonka absolute-like and maple topnotes. |
| Perfume composition of Example II. | Patchouli, with sweet, maple, tonka, honey, coumarin-like and cherry undertones, with sweet, honey, coumarin, tonka absolute-like and maple topnotes |

EXAMPLE IV

Perfumed Liquid Detergents

Concentrated liquid detergents (Lysine salt of n-dodecylbenzene sulfonic acid as more specifically described in U.S. Pat. No. 3,948,818 issued on Apr. 6, 1976) with aroma nuances as set forth in Table I of Example III are prepared containing 0.10%, 0.15%, 0.20%, 0.25%, 0.30% and 0.35% of the substance set forth in Table I of Example III. They are prepared by adding and homogeneously mixing the appropriate quantity of substance set forth in Table I of Example III below in the liquid detergent. The detergents all possess excellent aromas as set forth in Table I of Example III, the intensity increasing with greater concentrations of substance as set forth in Table I of Example III.

EXAMPLE V

Preparation of Colognes and Handkerchief Perfumes

Compostions as set forth in Table I of Example III are incorporated into colognes at concentrations of 2.0%, 2.5%, 3.0%, 3.5%, 4.0%, 4.5% and 5.0% in 80%, 85%, 90% and 95% aqueous food grade ethanol solutions, and into handkerchief perfumes at concentrations of 15%, 20%, 25% and 30% (in 80%, 85%, 90% and 95% aqueous food grade ethanol solutions). Distinctive and definitive fragrances as set forht in Table I of Example III are imparted to the colognes and to the handkerchief perfumes at all levels indicated.

EXAMPLE VI

Preparation of Soap Compositions

One hundred grams of soap chips [per sample] (IVORY ®, produced by the Procter & Gamble Company of Cincinnati, Ohio), are each mixed with one gram samples of substances as set forth in Table I of Example III until homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table I of Example III.

EXAMPLE VII

Preparation of Solid Detergent Composition

Detergents are prepared using the following ingredients according to Example I of Canadian Patent No. 1,007,948:

| Ingredient | Percent by Weight |
| --- | --- |
| "NEODOL ® 45-11 (a $C_{14}$–$C_{15}$ alcohol ethoxylated with 11 moles of ethylene oxide) | 12 |
| Sodium carbonate | 55 |
| Sodium citrate | 20 |
| Sodium sulfate, water brighteners | q. s. |

This detergent is a phosphate-free detergent. Samples 100 grams each of this detergent are admixed with 0.10, 0.15, 0.20 and 0.25 grams of each of the substances as set forth in Table I of Example III. Each of the detergent samples has an excellent aroma as indicated in Table I of Example III.

EXAMPLE VIII

Utilizing the procedure of Example I at column 15 of U.S. Pat. No. 3,632,396, non-woven cloth substrates useful as drier-added fabric softening articles of manufacture are prepared wherein the substrate, the substrate coating the outer coating and the perfuming material are as follows:
1. A water "dissolvable" paper ("Dissolvo Paper");
2. Adogen 448 (m.p. about 140° F.) as the substrate coating; and
3. An outer coating having the following formulation (m.p. about 150° F.):
   57%—$C_{20-22}$HAPS
   22%—isopropyl alcohol
   20%—antistatic agent
   1%—of one of the substances as set forth in Table I of Example III.

Fabric softening compositions prepared according to Example I at column 15 of U.S. Pat. No. 3,632,396 having aroma characteristics as set forth in Table I of Example III, consist of a substrate coating having a weight of about 3 grams per 100 square inches of substrate; a first coating on the substrate coating consisting of about 1.85 grams per 100 square inches of substrate; and an outer coating coated on the first coating consisting of about 1.4 grams per 100 square inches of substrate One of the substances of Table I of Example III is admixed in each case with the outer coating mixture, thereby providing a total aromatized outer coating weight ratio to substrate of about 0.5:1 by weight of the substrate. The aroma characteristics are imparted in a pleasant manner to the head space in a dryer on operation thereof in each case using said drier-added fabric softener non-woven fabrics and these aroma characteristics are described in Table I of Example III.

EXAMPLE IX

Hair Spray Formulation

The following hair spray formulation is prepared by first dissolving PVP/VA E-735 copolymer manufactured by the GAF Corporation of 140 West 51st Street, New York, N.Y., in 91.62 grams of 95% food grade ethanol, 8.0 grams of the polymer is dissolved in the alcohol. The following are added to the PVP/VA alcohol solution:

| Ingredient | Percent by Weight |
| --- | --- |
| Dioctyl sebacate | 0.05 |
| Benzyl alcohol | 0.10 |
| Dow Corning 473 fluid (prepared by the Dow Corning Corporation) | 0.03 |
| TWEEN ® 20 surfactant (prepared by ICI America Corporation) | |
| One of the perfumery substances as set forth in Table I of Example III | 0.10 |

The perfuming substances as set forth in Table I of Example III add aroma characteristics as set forth in Table I of Example III which are rather intense and aesthetically pleasing to the users of the soft-feel, good hold pump hair sprays.

EXAMPLE X

Conditioning Shampoos

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation)(1.4 weight percent). The resulting melt is admixed with Stepanol WAT produced by the Stepan Chemical Company (35.0 weight percent). The resulting mixture is heated to 60° C. and mixed until a clear solution is obtained (at 60° C.).

GAFQUAT ® 755N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 disterate produced by Armak Corporation.

The resulting material is then mixed and cooled to 45° C. and 0.3 weight percent of perfuming substance as set forth in Table I of Example III is added to the mixture. The resulting mixture is cooled to 40° C. and blending is carried out for an additional one hour in each case. At the end of this blending period, the resulting material has a pleasant fragrance as indicated in Table I of Example III.

What is claimed is:
1. The compound having the structure:

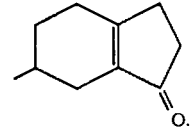

2. A perfume composition comprising a perfume base and intimately admixed therewith the compound defined according to claim 1 in an aroma imparting, augmenting or enhancing amount.

3. A cologne comprising ethanol, water and a perfuming amount of the compound of claim 1.

4. A perfumed article comprising a perfumed article base and intimately admixed therewith the compound defined according to claim 1.

5. A detergent comprising a detergent base and intimately admixed therewith an aroma augmenting, imparting or enhancing quantity of the compound of claim 1.

6. A process for augmenting or enhancing the aroma of a perfume composition, cologne or perfumed article comprising the step of intimately admixing with said perfumed composition, cologne or perfumed article an aroma augmenting or enhancing quantity of the compound defined according to claim 1.

7. A perfumed polymer comprising a polymer having pores therein and present in the pores an aroma imparting, augmenting or enhancing quantity of the compound defined according to claim 1.

* * * * *